United States Patent [19]
Cone

[11] Patent Number: 5,614,363
[45] Date of Patent: Mar. 25, 1997

[54] TSH RECEPTOR

[75] Inventor: Roger Cone, Portland, Oreg.

[73] Assignee: New England Medical Center Hospitals, Inc., Boston, Mass.

[21] Appl. No.: 146,835

[22] Filed: Oct. 29, 1993

Related U.S. Application Data

[63] Continuation-in-part of Ser. No. 565,669, Aug. 10, 1990, abandoned, which is a continuation-in-part of Ser. No. 469,925, Jan. 25, 1990, abandoned.

[51] Int. Cl.⁶ .......................... C07K 14/705; C12N 5/10; C12Q 1/68
[52] U.S. Cl. .................. 435/6; 435/7.1; 435/7.2; 435/252.3; 435/320.1; 435/69.1; 530/350; 536/23.5
[58] Field of Search .......................... 530/350; 435/69.1, 435/6; 536/23.5; 436/536, 507, 506

[56] References Cited

FOREIGN PATENT DOCUMENTS

| WO-A- | | |
|---|---|---|
| 9013643 | 11/1990 | European Pat. Off. . |
| WO-A-9110735 | 6/1991 | European Pat. Off. . |
| WO-A-9109121 | 6/1991 | European Pat. Off. . |
| WO-A-9109137 | 6/1991 | European Pat. Off. . |
| 90913766 | 5/1992 | European Pat. Off. . |

OTHER PUBLICATIONS

Thomas et al. *Methods in Enzymology* 182:499–521 (1990).
Kajimura et al *DNA* 2(3):175–182 (1983).
Rees Smith et al *J. Endocrinol. Invest.* 8:175 (1985).
Rees Smith et al., 9 Endocrine Reviews 106, 1988.
Libert et al., Biochemical And Biophysical Research Communications 165(3):1250–1255, 1989.
Nagayama et al., Biochemical and Biophysical Research Communications 165(3):1184–1190, 1989.
Parmentier et al., Science 246:1620, 1989.
Katani et al., Metabolism 24(8):959, 1975.
Verrier et al., Eur. J. Biochem. 74, 243–252, 1977.
Reid, J. Pediatrics, 56(5):658, 1960.
McFarland et al., Science, 245:494, 1989.
Loosefelt et al., Science 245:525, 1989.
Beamer et al., Science 212:61, 1981.
de The et al., Nature, 330:667, 1987.
Kohn et al., Biochemical Actions of Hormones, 12:457, 1985.
Frazier–Seabrook et al., 64th Meeting of the American Thyroid Association, 1989, Abstract No. T-51.
Chan et al., Acta Endocrinologica, vol. 115, 1987, pp. 166–172.
Islam et al., Clinical Research, vol. 29, No. 2, Apr. 1981, p. 294A.
Endocrinology, vol. 110, No. 4, Apr. 1982, pp. 1381–1391.

*Primary Examiner*—John Ulm
*Attorney, Agent, or Firm*—Fish & Richardson P.C.

[57] ABSTRACT

A protein having the biological activity of a mammalian TSH receptor, and purified nucleic acid encoding such a protein.

13 Claims, 15 Drawing Sheets

| | | | | | | | | | | | | | | |
|---|---|---|---|---|---|---|---|---|---|---|---|---|---|---|
|AAG|GAG|CTG|AGT|GGC|TGT|TGG|AAA|CCT|GAG|CCC|AAT|GAC|TTC|GCC|CCT|
|Lys|Glu|Leu|Ser|Gly|Cys|Trp|Lys|Pro|Asp|Pro|Asn|Asp|Phe|Ala|Pro|
|1| | |  |5| | | |  |10| | | |  |15| |

```
AAG GAG CTG AGT GGC TGT TGG AAA CCT GAG CCC AAT GAC TTC GCC CCT
Lys Glu Leu Ser Gly Cys Trp Lys Pro Asp Pro Asn Asp Phe Ala Pro
 1           5                   10                  15

GAT GGT GCC GTG CGC TGT CCT GGC CCT CGA GCC GGC CTC GCC AGA CTA
Asp Gly Ala Val Arg Cys Pro Gly Pro Arg Ala Gly Leu Ala Arg Leu
            20                  25                  30

TCT CTC ACC TAT CTC CCT GTC AAA GTA ATT CCA TCA CAA GCT TTC AGG
Ser Leu Thr Tyr Leu Pro Val Lys Val Ile Pro Ser Gln Ala Phe Arg
            35                  40                  45

GGA CTT AAT GAG GTC GTA AAA ATT GAA ATC TCT CAG AGT GAT TCC CTG
Gly Leu Asn Glu Val Val Lys Ile Glu Ile Ser Gln Ser Asp Ser Leu
        50                  55                  60

GAA AGG ATA GAA GCT AAT GCT TTG ACA ACC TCC TCA ATT TGT CTG AAC
Glu Arg Ile Glu Ala Asn Ala Leu Thr Thr Ser Ser Ile Cys Leu Asn
65                  70                  75                  80

TAC TTG ATC CAG AAC ACC AAA AAC CTG GTA TAC ATT GAA CCT GGT GCT
Tyr Leu Ile Gln Asn Thr Lys Asn Leu Val Tyr Ile Glu Pro Gly Ala
                85                  90                  95

TTT ACA AAC CTC CCT GGG CAA AAA TAC CTG AGC ATG TGT AAC ACA GCT
Phe Thr Asn Leu Pro Gly Gln Lys Tyr Leu Ser Met Cys Asn Thr Ala
            100                 105                 110

ATC CGA ACC CTT CCA GAT GTT ACG AAG ATC TCC TCC TCT GAA TTT AAT
Ile Arg Thr Leu Pro Asp Val Thr Lys Ile Ser Ser Ser Glu Phe Asn
            115                 120                 125

TTC ACT CTG GAA ATC TGT GAT AAC TTA CAC ATA ACC ACC ATA CCC GGG
Phe Thr Leu Glu Ile Cys Asp Asn Leu His Ile Thr Thr Ile Pro Gly
        130                 135                 140

AAT GCT TTC CAA GGG ATG AAT AAC GAG TCT GTC ACA CTA AAA CTG TAT
Asn Ala Phe Gln Gly Met Asn Asn Glu Ser Val Thr Leu Lys Leu Tyr
145                 150                 155                 160

GGA AAT GGA TTT GAA GAA GTA CAA AGC CAT GCA TTC AAT GGG ACG ACT
Gly Asn Gly Phe Glu Glu Val Gln Ser His Ala Phe Asn Gly Thr Thr
            165                 170                 175

CTA ATC TCG CTG GAG CTA AAA CAT CTA CCT GGA GAA GAT GCA CAG TGG
Leu Ile Ser Leu Glu Leu Lys His Leu Pro Gly Glu Asp Ala Gln Trp
            180                 185                 190

AGC CTT CCA GGG TGC CAC AGG CCC TAC CAT CCT GGA CAC GT
Ser Leu Pro Gly Cys His Arg Pro Tyr His Pro Gly His
        195                 200                 205
```

FIG. 1

CAGACACTGGCAAGCCGCAGAAGCCCAGTTCGCCGGCC

| ATG | AAG | CAG | CGG | TTC | TCG | CCG | CTG | CAG | CTG | CTG | AAG | CTG | CTG | CTG |
|---|---|---|---|---|---|---|---|---|---|---|---|---|---|---|
| Met | Lys | Gln | Arg | Phe | Ser | Pro | Leu | Gln | Leu | Leu | Lys | Leu | Leu | Leu |
| 1 | | | | 5 | | | | | 10 | | | | | 15 |

| CTG | CAG | GCG | CCG | CTG | CCA | CGA | GCG | CTG | CGC | AGG | CTC | TGC | CCT | GAG | CCC |
|---|---|---|---|---|---|---|---|---|---|---|---|---|---|---|---|
| Leu | Gln | Ala | Pro | Leu | Pro | Arg | Ala | Leu | Arg | Arg | Leu | Cys | Pro | Glu | Pro |
| | | | 20 | | | | | 25 | | | | | 30 | | |

| TGC | AAC | TGC | GTG | CCC | GAC | GGC | GCC | CTG | CGT | GCC | CCG | GCC | CCA | CGG | CCG |
|---|---|---|---|---|---|---|---|---|---|---|---|---|---|---|---|
| Cys | Asn | Cys | Val | Pro | Asp | Gly | Ala | Leu | Arg | Ala | Pro | Ala | Pro | Arg | Pro |
| | 1 | 35 | | | | | 40 | | | | | 45 | | | |

| TCC | ACT | CGA | CTA | TCA | CTT | GCC | TAC | CTC | CCT | GTC | AAA | GTG | ATC | CCA | TCT |
|---|---|---|---|---|---|---|---|---|---|---|---|---|---|---|---|
| Ser | Thr | Arg | Leu | Ser | Leu | Ala | Tyr | Leu | Pro | Val | Lys | Val | Ile | Pro | Ser |
| | | 50 | | | | | 55 | | | | | 60 | | | |

| CAA | AGT | TTC | AGA | GGA | CTT | AAT | GAG | GTC | ATA | AAA | ATT | GAA | ATC | TCT | CAG |
|---|---|---|---|---|---|---|---|---|---|---|---|---|---|---|---|
| Gln | Ser | Phe | Arg | Gly | Leu | Asn | Glu | Val | Ile | Lys | Ile | Glu | Ile | Ser | Gln |
| 65 | | | 2 | 70 | | | | | 75 | | | | | | 80 |

| ATT | GAT | TCC | CTG | GAA | AGG | ATA | GAA | GCT | AAT | GCC | TTT | GAC | AAC | CTC | CTC |
|---|---|---|---|---|---|---|---|---|---|---|---|---|---|---|---|
| Ile | Asp | Ser | Leu | Glu | Arg | Ile | Glu | Ala | Asn | Ala | Phe | Asp | Asn | Leu | Leu |
| ▼ | | | | 85 | | | | | 90 | | | | | 95 | |

| AAT | TTG | TCT | GAA | ATA | CTG | ATC | CAG | AAC | ACC | AAA | AAT | CTG | AGA | TAC | ATT |
|---|---|---|---|---|---|---|---|---|---|---|---|---|---|---|---|
| Asn | Leu | Ser | Glu | Ile | Leu | Ile | Gln | Asn | Thr | Lys | Asn | Leu | Arg | Tyr | Ile |
| 3 | | | | 100 | | | | | 105 | | | | | 110 | |

| GAG | CCC | GGA | GCA | TTT | ATA | AAT | CTT | CCC | CGA | TTA | AAA | TAC | TTG | AGC | ATC |
|---|---|---|---|---|---|---|---|---|---|---|---|---|---|---|---|
| Glu | Pro | Gly | Ala | Phe | Ile | Asn | Leu | Pro | Arg | Leu | Lys | Tyr | Leu | Ser | Ile |
| | | 115 | | | | | 120 | | | | | 125 | | | |
| | | | | 4 | | | | | | | | | | | |

| TCT | AAC | ACA | GGC | ATC | AGA | AAG | TTT | CCA | GAT | GTT | ACG | AAG | GTC | TTC | TCC |
|---|---|---|---|---|---|---|---|---|---|---|---|---|---|---|---|
| Ser | Asn | Thr | Gly | Ile | Arg | Lys | Phe | Pro | Asp | Val | Thr | Lys | Val | Phe | Ser |
| | 130 | | | | 135 | | | | | 140⁻ | | | | | |

| TCT | GAA | TCA | AAT | TTC | AAT | CTG | GAA | ATT | TGT | GAT | AAC | TTA | CAC | ATA | ACC |
|---|---|---|---|---|---|---|---|---|---|---|---|---|---|---|---|
| Ser | Glu | Ser | Asn | Phe | Asn | Leu | Glu | Ile | Cys | Asp | Asn | Leu | His | Ile | Thr |
| 145 | 5 | | | | 150 | | | | | 155 | | | | | 160 |
| | | | | | | | | | | ▼ | | | | | |

| ACC | ATA | CCA | GGA | AAT | GCT | TTT | CAA | GGG | ATG | AAT | AAT | GAA | TCT | GTA | ACA |
|---|---|---|---|---|---|---|---|---|---|---|---|---|---|---|---|
| Thr | Ile | Pro | Gly | Asn | Ala | Phe | Gln | Gly | Met | Asn | Asn | Glu | Ser | Val | Thr |
| | | | | 165 | | | | 6 | 170 | | | | | 175 | |

CTC
Leu

CCATGGCAAA......TAAAAAATTGC

FIG. 2A

```
                                                              ▼
AAA CTA TAT GGA AAT GGA TTT GAA GAA GTA CAA AGT CAT GCA TTC AAT
Lys Leu Tyr Gly Asn Gly Phe Glu Glu Val Gln Ser His Ala Phe Asn
1               5                   10                  15

GGG ACG ACA CTG ACT TCA CTG GAG CTA AAG GAA AAC GTA CAT CTG GAG
Gly Thr Thr Leu Thr Ser Leu Glu Leu Lys Glu Asn Val His Leu Glu
            20      7           25              30

AAG ATG CAC AAT GGA GCC TTC CGT GGG GCC ACA GGG CCG AAA ACC TTG
Lys Met His Asn Gly Ala Phe Arg Gly Ala Thr Gly Pro Lys Thr Leu
        35                  40      8       45

GAT ATT TCT TCC ACC AAA TTG CAG GCC CTG CCG AGC TAT GGC CTA GAG
Asp Ile Ser Ser Thr Lys Leu Gln Ala Leu Pro Ser Tyr Gly Leu Glu
    50              55                  60                  9

TCC ATT CAG AGG CTA ATT GCC ACG TCA TCC TAT TCT CTA AAA AAA TTG
Ser Ile Gln Arg Leu Ile Ala Thr Ser Ser Tyr Ser Leu Lys Lys Leu
65              70              75                          80

CCA TCA AAA CAA ACA TTT GTC AAT CTC CTG AGG GCC ACG CTT CAT TAC
Pro Ser Lys Gln Thr Phe Val Asn Leu Leu Arg Ala Thr Leu His Tyr
        10 85                   90                  95
                                                              ▼
CCC AGC CAC TGC TGT GCA TTT AGA AAC TTG CCA ACG AAA GAG CTA AAC
Pro Ser His Cys Cys Ala Phe Arg Asn Leu Pro Thr Lys Glu Leu Asn
            100             105                 110

TTC
Phe
11

TTAGAGGGAA......GTGTAATAGACAGAATTTT
                        ▼
TCA CAT TCC ATT TCT GAA AAC TTT TCC AAA CAA TGT GAA AGC ACA GTA
Ser His Ser Ile Ser Glu Asn Phe Ser Lys Gln Cys Glu Ser Thr Val
1               5                   10      12          15

AGG AAA
Arg Lys

GTGAGTAACA......TGCTGAG
AGT GAA CTG AGT GGC TGG GAC TAT GAA TAT GGT TTC TGC TTA CCC AAG
Ser Glu Leu Ser Gly Trp Asp Tyr Glu Tyr Gly Phe Cys Leu Pro Lys
1               5                   10 13               15

ACA CCC CGA TGT GCT CCT GAA CCA GAT GCT TTT AAT CCC TGT GAA GAC
Thr Pro Arg Cys Ala Pro Glu Pro Asp Ala Phe Asn Pro Cys Glu Asp
            20                  25                  30

ATT ATG GGC TAT GAC TTC CTT AGG GTC CTG ATT TGG CTG ATT AAT ATT
Ile Met Gly Tyr Asp Phe Leu Arg Val Leu Ile Trp Leu Ile Asn Ile
    14 35               40                  45
```

FIG. 2B

```
                                   I
CTA GCC ATC ATG GGA AAC ATG ACT CTT CTT TTT GTT CTC CTG ACA AGT
Leu Ala Ile Met Gly Asn Met Thr Leu Leu Phe Val Leu Leu Thr Ser
        50                  55                  60

CGT TAC AAA CTT ACA GTG CCT CGT TTT CTC ATC TGC AAT CTC TCC TTT
Arg Tyr Lys Leu Thr Val Pro Arg Phe Leu Ile Cys Asn Leu Ser Phe
65              70                  75                      80
        II
GCA GAC TTT TGC ATG GGG CTC TAT CTG CTG CTC ATA GCC TCA GTT GAT
Ala Asp Phe Cys Met Gly Leu Tyr Leu Leu Leu Ile Ala Ser Val Asp
                85                  90                  95

TCC CAA ACC AAG GGC CAG TAC TAT AAC CAT GCC ATA GAC TGG CAG ACA
Ser Gln Thr Lys Gly Gln Tyr Tyr Asn His Ala Ile Asp Trp Gln Thr
                    100                 105                 110

GGG AGT GGG TGC AGC ACT GCT GGC TTT TTC ACT GTA TTA GCA AGT GAA
Gly Ser Gly Cys Ser Thr Ala Gly Phe Phe Thr Val Leu Ala Ser Glu
                115                 120                 125
                    III
CTT TCT GTC TAC ACC CTC ACC GTC ATC ACT CTA GAA AGA TGG CAC ACC
Leu Ser Val Tyr Thr Leu Thr Val Ile Thr Leu Glu Arg Trp His Thr
        130                 135                 140

ATC ACC TAT GCT ATT CAC CTG GAC CAA AAG CTG CGA TTA AGA CAT GCC
Ile Thr Tyr Ala Ile His Leu Asp Gln Lys Leu Arg Leu Arg His Ala
145                 150                 155                 160
                                    IV
ATT CTG ATT ATG CTT GGA GGC TGG CTC TTT TCT TCT CTA ATT GCT ATG
Ile Leu Ile Met Leu Gly Gly Trp Leu Phe Ser Ser Leu Ile Ala Met
                165                 170                 175

TTG CCC CTT GTC GGG GTC AGC AAT TAC ATG AAG GTC AGT ATT TGC TTC
Leu Pro Leu Val Gly Val Ser Asn Tyr Met Lys Val Ser Ile Cys Phe

CCC ATG GAT GTG GAA ACC ACT CTC TCA CAA GTC TAT ATA TTA ACC ATC
Pro Met Asp Val Glu Thr Thr Leu Ser Gln Val Tyr Ile Leu Thr Ile
                                            V
CTG ATT CTC ATT GTG GTG GCC TTA ATA ATT TGT GCT TGC TAC ATT
Leu Ile Leu Ile Val Val Ala Phe Leu Ile Ile Cys Ala Cys Tyr Ile

AAA ATT TAT TTT GCA TGG CGA AAC CCA GAA TTA ATG GCT ACC AAT AAA
Lys Ile Tyr Phe Ala Val Arg Asn Pro Glu Met Ala Thr Asn Lys Asp
            180                 185                 190
                                                        VI
GCT AAG AAA ATG GCA ATC CTC ATC TTC ACC GAT TTT ACC TGC ATG GCA
Ala Lys Lys Met Ala Ile Leu Ile Phe Thr Asp Phe Thr Cys Met Ala
        210                 215                 220

CCT ATC TCT TTT TTT GCC ATC TCA GCT GCC TTC AAA GTA CCT CTT ATC
Pro Ile Ser Phe Phe Ala Ile Ser Ala Ala Phe Lys Val Pro Leu Ile
225                 230                 235                 240
```

FIG. 2C

```
                                                                              VII
ACA GTA ACC AAC TCT AAA GTT TTA CTG GTT CTT TTT TAT CCC ATC AAT
Thr Val Thr Asn Ser Lys Val Leu Leu Val Leu Phe Tyr Pro Ile Asn
                    245             250             255

TCT TGT GCC AAT CCA TTT CTG TAT GCA ATA TTC ACT AAG ACA TTC CAA
Ser Cys Ala Asn Pro Phe Leu Tyr Ala Ile Phe Thr Lys Thr Phe Gln
            260             265             270

AGA GAT TTC TTT CTT TTG CTG AGC AAA TTT GGC TGC TGT AAA CGT CGG
Arg Asp Phe Phe Leu Leu Leu Ser Lys Phe Gly Cys Cys Lys Arg Arg
            275             280             285

GCT GAT CCT CTT TAT AGA AGG AAA GAT TTT TCA GCT TAC ACC TCC AAC
Ala Asp Pro Leu Tyr Arg Arg Lys Asp Phe Ser Ala Tyr Thr Ser Asn
            290             295         A   300

TGC AAA AAT GGC TTC ACT GGA TCA AAT AAG CCT TCT CAA TCC ACC TTG
Cys Lys Asn Gly Phe Thr Gly Ser Asn Lys Pro Ser Gln Ser Thr Leu
305             310             315         C   320

AAG TTG TCC ACA TTG CAC TGT CAA GGT ACA GCT CTC CTA GAC AAG ACT
Lys Leu Ser Thr Leu His Cys Gln Gly Thr Ala Leu Leu Asp Lys Thr
            325             330             335

CGC TAC ACA GAG TGT TAA
Arg Tyr Thr Glu Cys
            340
CTGTTACATCAGTAACTGCATTATTGAATTGTTCTTAAACCTGTAAA
```

FIG. 2D

```
3865
AAAAAATTACCTGTACCAGTAATTTTAACATAAAGGGTTGGATTTAGGAAATTATTTATTTTTAGGTAC 2260
ATTAGGCAAGAGACCTCTACCAGTAGAAAGTGTAGTGTGTAGTCTATGACCACTGCCACACTAAAAACT 2329
ATTGTCATTGT                                                          2467
4008 TACATTGGCATAAATACTGAAGTTGAGAGTGTTTTTTATAGAAATTTTGACACAGTAATTTTGTTTGAT
2536
GAATCTTTTAAAAAACTGAGGAGGTATTTTGCATATCTTTTTTTTCATTTTCGTAATTTGTATTGCATT 2605
CTATA                                                                2610

4151
AAAATATTAGTTCATAACAGATCAGAAATTTAAAATAACTGGCCTTTTTCCTCAGGTAGTTTGAAAAAC 2679
ACACTCTAGAGATGCACTGTCCAATCCGGTAGCCACTAGCACATGTGGCTAAATTAAAATTAAATAAAA 2748
TGAGA                                                                2753

4294
AATGTAGTTTCTCAGTTGCACTAGCCACGTTTCAAGTTCTCAATGGCTACGTGTGACTAGTGCTTACCA 2822
TACTGGACAGCACAGACACAGAATATTTTCATCACCACAGAAAGTTCTATCTGTTCTATTATAGAGACT 2891
TTTAT

4437
CTATGCCCTATCTGGATTCTACTTATTTATAATTTAAGGTAAACATCTGAAAGCACATTTCAGCCTATT 2960
TGCTTAGTGAAACATTAAGCTGTAGACTGTAAACTCCTCGTGAGTAGGAACCCTGTCTCAGTGCATTTT 3029
GTTTT                                                                3034

4580
CCTGCTTCCTACCTCAAGATCTTGGCAATGGTACACTACAAATGTGCTGAGTTAGAATTACTCTGAAGTT 3103
ATGAAACATATAATGAAAACAATTTTTTCTAGAGCTTATATTTTATTTGAATGAAATAAAATGTTTAAA 3172
ATA                                                                  3175

4723
TTTAAAAATAAAAAAAAAA                                                  3194
```

FIG. 2E

```
              Eco RI          a              a   a        aa  a
5' OLIGO  acagaattc ggcttttcttaccgtctttgcctccga
                         g  c c       g  g c g gg
                         t            t  t   t  t
``` degeneracy = 32,768

```
              Hind III
                          a a       a    a          a
3' OLIGO  acaaagctt aaacctaaatcggcgccatacacgtaaa
                    g  gg g    g  g      g  g  g
                    t   t t    t  t      t     t
``` degeneracy = 24,576

PCR FRAGMENT (TSH RECEPTOR TRANSMEMBRANE DOMAINS 3-6)
PARTIAL SEQUENCE

| | | | | | | | | | | | | | | |
|---|---|---|---|---|---|---|---|---|---|---|---|---|---|---|
|GGG|TTC|TTC|ACG|GTG|TTT|GCG|AGC|GAG|CTG|TCT|GTG|TAC|ACG|CTG|ACG|
|Gly|Phe|Phe|Thr|Val|Phe|Ala|Ser|Glu|Leu|Ser|Val|Tyr|Thr|Leu|Thr|
|1| | | |5| | | | |10| | | | |15| |

GTC ATC ACC TTG GAG CGC TGG CAC GCC ATC ACC TTC GCC ATG CGC CTG
Val Ile Thr Leu Glu Arg Trp His Ala Ile Thr Phe Ala Met Arg Leu
            20                  25                  30

GAC CGC AAG ATC CGC CTC TGG CAC GCC TAC GTC ATC ATG CTG GGG GGC
Asp Arg Lys Ile Arg Leu Trp His Ala Tyr Val Ile Met Leu Gly Gly
                35                  40                  45

TGG GTT TGC TGC TTC CTG CTC GCC CTG CTC CCT TTC CTC CCA ATA AGC
Trp Val Cys Cys Phe Leu Leu Ala Leu Leu Pro Phe Leu Pro Ile Ser
        50                  55                  60

AGC TAT GCC AAC CTG CGC ATC TGC CTG CCC ATG GAC ACC GAG
Ser Tyr Ala Asn Leu Arg Ile Cys Leu Pro Met Asp Thr Glu
65                  70                  75

HUMAN PCR FRAGMENT (TSH RECEPTOR TRANSMEMBRANE DOMAINS 3-6)

GTT TTT CGT AGC GAG TTA TCG GTG TAT ACG CTG ACG GTC ATC ACC CTG
Val Phe Arg Ser Glu Leu Ser Val Tyr Thr Leu Thr Val Ile Thr Leu
1               5                   10                  15

GAG CGC TGG TAT GCC ATC ACC TTC GCG ATG CGC CTG GAC CGG AAG ATC
Glu Arg Trp Tyr Ala Ile Thr Phe Ala Met Arg Leu Asp Arg Lys Ile
                20                  25                  30

CGC CTC AGG CAC GCA TGT CGG ATC ACC TTC GCC ATG CGC CTG GAC CGG
Arg Leu Arg His Ala Cys Arg Ile Thr Phe Ala Met Arg Leu Asp Arg
        35                  40                  45

AAG ATC CGC CTC AGG CAC GCA TGT CGG ATC ATG GTT GGG GGC TGG GTT
Lys Ile Arg Leu Arg His Ala Cys Arg Ile Met Val Gly Gly Trp Val
    50                  55                  60

TGC TGC TTC CTT CTC GCC CTG CTT CCT TTG GTG GGA ATA AGT AGC TAT
Cys Cys Phe Leu Leu Ala Leu Leu Pro Leu Val Gly Ile Ser Ser Tyr
65                  70                  75                  80

GCC AAA GTC AGT ATC TGC CTG CCC ATG GAC ACC GAG ACC CCT CTT GCT
Ala Lys Val Ser Ile Cys Leu Pro Met Asp Thr Glu Thr Pro Leu Ala
                85                  90                  95

CTG GCA TAT ATT GTT TTT GTT CTG ACG GTC AAC ATA
Leu Ala Tyr Ile Val Phe Val Leu Thr Val Asn Ile
            100                 105

FIG. 5A

```
GTT GGC TTC GTC ATC GTC TGC TGC TGT TAT GTG AAG ATC TAC ATC ACA
Val Gly Phe Val Ile Val Cys Cys Cys Tyr Val Lys Ile Tyr Ile Thr
1               5                   10                  15

GTC CGA AAT CCG CAC AAC CCA GGG GAC AAA GAT ACC AAA ATT GCC AAG
Val Arg Asn Pro His Asn Pro Gly Asp Lys Asp Thr Lys Ile Ala Lys
                20                  25                  30

AGG ATG GCT GTG TTG ATC TTC ACC GAC TTC ACG TGC ATG GCC CCC
Arg Met Ala Val Leu Ile Phe Thr Asp Phe Thr Cys Met Ala Pro
        35                  40                  45
```

FIG. 5B

TAATACGACTCACTATAGGCGAATTAAGCGATTTCGGAGGATGGAGAAATAGCCCCGAGTCCCGTGGAA
A

| | | | | | | | | | | | | | | |
|---|---|---|---|---|---|---|---|---|---|---|---|---|---|---|
| ATG | AGG | CCG | GCG | GAC | TTG | CTG | CAG | CTG | GTG | CTG | CTG | CTC | GAC | CTG | CCC |
| Met | Arg | Pro | Ala | Asp | Leu | Leu | Gln | Leu | Val | Leu | Leu | Leu | Asp | Leu | Pro |
| 1 | | | | 5 | | | | | 10 | | | | | 15 | |

AGG GAC CTG GGC GGA ATG GGG TGT TCG TCT CCA CCC TGC GAG TGC CAT
Arg Asp Leu Gly Gly Met Gly Cys Ser Ser Pro Pro Cys Glu Cys His
              20              25              30

CAG GAG|GAG GAC TTC AGA GTC ACC TGC AAG GAT ATT CAA CGC ATC CCC
Gln Glu|Glu Asp Phe Arg Val Thr Cys Lys Asp Ile Gln Arg Ile Pro
       |35              40              45

AGC TTA CCG CCC AGT ACG CAG ACT CTG AAG CTT ATT GAG ACT CAC|CTG
Ser Leu Pro Pro Ser Thr Gln Thr Leu Lys Leu Ile Glu Thr His|Leu
    50           1   55              60
                                      ▼

AGA ACT ATT CCA AGT CAT GCA TTT TCT AAT CTG CCC AAT ATT TCC AGA
Arg Thr Ile Pro Ser His Ala Phe Ser Asn Leu Pro Asn Ile Ser Arg
65              70              75  2           80

ATC TAC GTA TCT ATA GAT GTG ACT|CTG CAG CAG CTG GAA TCA CAC TCC
Ile Tyr Val Ser Ile Asp Val Thr|Leu Gln Gln Leu Glu Ser His Ser
            85                 90                  95
        ▼

TTC TAC AAT TTG AGT AAA GTG ACT CAC ATA GAA ATT CGG AAT ACC AGG
Phe Tyr Asn Leu Ser Lys Val Thr His Ile Glu Ile Arg Asn Thr Arg
            100 3           105             110
▼

AAC|TTA ACT TAC ATA GAC CCT GAT GCC CTC AAA GAG CTC CCC CTC CTA
Asn|Leu Thr Tyr Ile Asp Pro Asp Ala Leu Lys Glu Leu Pro Leu Leu
   115              120                 125 4

AAG TCC TTG GCA TTT TCA AAC ACT GGA|CTT AAA ATG TTC CCT GAC CTG
Lys Ser Leu Ala Phe Ser Asn Thr Gly|Leu Lys Met Phe Pro Asp Leu
    130             135             140

ACC AAA GTT TAT TCC ACT GAT ATA TTC TTT ATA CTT GAA ATT ACA GAC
Thr Lys Val Tyr Ser Thr Asp Ile Phe Phe Ile Leu Glu Ile Thr Asp
145             150 5           155             160

AAC CCT TAC|ATG ACG TCA ATC CCT GTG AAT GCT TTT CAG GGA CTA TGC
Asn Pro Tyr|Met Thr Ser Ile Pro Val Asn Ala Phe Gln Gly Leu Cys
           165             170             175 6
▼

AAT GAA ACC TTG ACA CTG AAG CTG TAC AAC AAT GGC|TTT ACT TCA GTC
Asn Glu Thr Leu Thr Leu Lys Leu Tyr Asn Asn Gly|Phe Thr Ser Val
        180             185             190

FIG. 6A

| | | | | | | | | | | | | | |
|---|---|---|---|---|---|---|---|---|---|---|---|---|---|
|CAA|GGA|TAT|GAT|TTC|TTT|GGG|ACA|AAG|CTG|GAT|GCT|GTT|TAC|CTA|AAC|
|Gln|Gly|Tyr|Asp|Phe|Phe|Gly|Thr|Lys|Leu|Asp|Ala|Val|Tyr|Leu|Asn|
| |  |195| | | | |200 7| | | |  |205| | | |

AAG AAT AAA TAC CTG ACA GTT ATT GAC AAA GAT GCA TTT GGA GGA GTA
Lys Asn Lys Tyr Leu Thr Val Ile Asp Lys Asp Ala Phe Gly Gly Val
       210                215                220

TAC AGT GGA CCA AGC TTG CTG GAC GTG TCT CAA ACC AGT GTC ACT GCC
Tyr Ser Gly Pro Ser Leu Leu Asp Val Ser Gln Thr Ser Val Thr Ala
225                 230                235                240
 8

CTT CCA TCC AAA GGC CTG GAG CAC CTG AAG GAA CTG ATA GCA AGA AAC
Leu Pro Ser Lys Gly Leu Glu His Leu Lys Glu Leu Ile Ala Arg Asn
                245         9   250                255

AGC TGG ACT CTT AAG AAA CTT GCA CTT TCC TTG AGT TTC CTT CAC CTC
Ser Trp Thr Leu Lys Lys Leu Ala Leu Ser Leu Ser Phe Leu His Leu
            260             265         10   270

ACA CGG GCT GAC CTT TCT TAC CCA AGC CAC TGC TGT GCT TTT AAG AAT
Thr Arg Ala Asp Leu Ser Tyr Pro Ser His Cys Cys Ala Phe Lys Asn
        275             280                 285     ▼ 11

CAG AAG AAA ATC AGA GGA ATC CTT GAG TCC TTG ATG TGT AAT GAG AGC
Gln Lys Lys Ile Arg Gly Ile Leu Glu Ser Leu Met Cys Asn Glu Ser
290                 295                     300

AGT ATC GAG ACG TTG CGC CAG AGA AAA TCT GTG AAT GCC TTG AAT AGC
Ser Ile Glu Thr Leu Arg Gln Arg Lys Ser Val Asn Ala Leu Asn Ser
305      12      310                315                     320

CCC CTC CAC CAG GAA TAT GAA GAG AAT CTG GGT GAC AGC ATT GTT GGG
Pro Leu His Gln Glu Tyr Glu Glu Asn Leu Gly Asp Ser Ile Val Gly
                325                 330   13        335

TAC AAG GAA AAG TCC AAG TTC CAG GAT ACT CAT AAC AAC GCT CAT TAT
Tyr Lys Glu Lys Ser Lys Phe Gln Asp Thr His Asn Asn Ala His Tyr
            340             345                 350

TAC GTC TTC TTT GAA GAA CAA GAG GAT GAT ATC ATT GGT TTT GGC CAG
Tyr Val Phe Phe Glu Glu Gln Glu Asp Asp Ile Ile Gly Phe Gly Gln
        355           14 360                365

GAG CTC AAA AAC CCC CAG GAA GAG ACT CTA CAA GCT TTT GAC AGC CAT
Glu Leu Lys Asn Pro Gln Glu Glu Thr Leu Gln Ala Phe Asp Ser His
        370             375                 380         15

TAT GAC TAC ACC ATA TGT GGG GAC AGT GAA GAC ATG GTG TGT ACC CCC
Tyr Asp Tyr Thr Ile Cys Gly Asp Ser Glu Asp Met Val Cys Thr Pro
385                 390                 395                 400

FIG. 6B

```
AAG TCC GAT GAG TTC AAC CCG TGT GAA GAC ATA ATG GGC TAC AAG TTC
Lys Ser Asp Glu Phe Asn Pro Cys Glu Asp Ile Met Gly Tyr Lys Phe
            405         16          410              I      415

CTG AGA ATT GTG GTG TGG TTC GTT AGT CTG GCT CTC CTG GGC AAT GTC
Leu Arg Ile Val Val Trp Phe Val Ser Leu Ala Leu Leu Gly Asn Val
        420              425              430

TTT GTC CTG CTT ATT CTC CTC ACC AGC CAC TAC AAA CTG AAC GTC CCC
Phe Val Leu Leu Ile Leu Leu Thr Ser His Tyr Lys Leu Asn Val Pro
        435              440          II      445

CGC TTT CTC ATG TGC AAC CTG GCC TTT GCG GAT TTC TGC ATG GGG ATG
Arg Phe Leu Met Cys Asn Leu Ala Phe Ala Asp Phe Cys Met Gly Met
    450              455              460

TAC CTG CTC CTC ATC GCC TCT GTA GAC CTC TAC ACT CAC TCT GAG TAC
Tyr Leu Leu Leu Ile Ala Ser Val Asp Leu Tyr Thr His Ser Glu Tyr
465              470              475              480

TAC AAC CAT GCC ATC GAC TGG CAG ACA GGC CCT GGG TGC AAC ACG GCT
Tyr Asn His Ala Ile Asp Trp Gln Thr Gly Pro Gly Cys Asn Thr Ala
            485              490       III          495

GGT TTC TTC ACT GTC TTT GCA AGC GAG TTA TCG GTG TAT ACG CTG ACG
Gly Phe Phe Thr Val Phe Ala Ser Glu Leu Ser Val Tyr Thr Leu Thr
            500              505              510

GTC ATC ACC CTG GAG CGC TGG TAT GCC ATC ACC TTC GCC ATG GCC CTG
Val Ile Thr Leu Glu Arg Trp Tyr Ala Ile Thr Phe Ala Met Ala Leu
        515              520              525   V

GAC CGG AAG ATC CGC CTC AGG CAC GCA TGT GCC TAC ATG CTT GGG GGC
Asp Arg Lys Ile Arg Leu Arg His Ala Cys Ala Tyr Met Leu Gly Gly
        530         IV      535              540

TGG GTT TGC TGC TTC CTT CTC GCC CTG CTT CCT TTG GTG GGA ATA AGT
Trp Val Cys Cys Phe Leu Leu Ala Leu Leu Pro Leu Val Gly Ile Ser
545              550              555              560

AGC TAT GCC AAA GTC AGT ATC TGC CTG CCC ATG GAC ACC GAG ACC CCT
Ser Tyr Ala Lys Val Ser Ile Cys Leu Pro Met Asp Thr Glu Thr Pro
            565              570     VI      575

CTT GCT CTG GCA TAT ATT GTT TTT GTT CTG ACG CTC AAC ATA GTT GCC
Leu Ala Leu Ala Tyr Ile Val Phe Val Leu Thr Leu Asn Ile Val Ala
        580              585              590

TTC GTC ATC GTC TGC TGC TGT TAT GTG AAG ATC TAC ATC ACA GTC CGA
Phe Val Ile Val Cys Cys Cys Tyr Val Lys Ile Tyr Ile Thr Val Arg
        595              600              605
```

FIG. 6C

```
AAT CCG CAC AAC CCA GGG GAC AAA GAT ACC AAA ATT GCC AAG AGG ATG
Asn Pro His Asn Pro Gly Asp Lys Asp Thr Lys Ile Ala Lys Arg Met
    610             615               620
                         VII

GCT GTG TTG ATC TTC ACC GAC TTC ACG TGC ATG GCC CCA ATC TCA TTC
Ala Val Leu Ile Phe Thr Asp Phe Thr Cys Met Ala Pro Ile Ser Phe
625                 630                635                 640

TAT GCT GTG TCA GCA ATT CTG AAC AAG CCT CTC ATC ACT GTT AGC AAC
Tyr Ala Val Ser Ala Ile Leu Asn Lys Pro Leu Ile Thr Val Ser Asn
                645               650                 655

TCC AAA ATC TTG CTG GTA CTC TTC TAT CCA ATT AAC TCC TGT GCC AAT
Ser Lys Ile Leu Leu Val Leu Phe Tyr Pro Ile Asn Ser Cys Ala Asn
            660                 665                 670

CCA TTC CTC TAT GCT ATT TTC ACC AAG GCC TTC CAG AGG GAT GTG TTC
Pro Phe Leu Tyr Ala Ile Phe Thr Lys Ala Phe Gln Arg Asp Val Phe
        675                 680                 685

ATC CTA CTC AGC AAG TTT GGC ATC TGT AAA CGC CAG GCT CAG GCA TAC
Ile Leu Leu Ser Lys Phe Gly Ile Cys Lys Arg Gln Ala Gln Ala Tyr
        690                 695                 700

CGG GGG CAG AGG GTT CCT CCA AAG AAC AGC ACT GAT ATT CAG GTT CAA
Arg Gly Gln Arg Val Pro Pro Lys Asn Ser Thr Asp Ile Gln Val Gln
705                 710             Ser 715                 720
                                     A

AAG GTT ACC CAC GAC ATG AGG CAG GGT CTC CAC AAC ATG GAA GAT GTC
Lys Val Thr His Asp Met Arg Gln Gly Leu His Asn Met Glu Asp Val
                725                 730    -            735

TAT GAA CTG ATT GAA AAC TCC CAT CTA ACC CCA AAG AAG CAA GGC CAA
Tyr Glu Leu Ile Glu Asn Ser His Leu Thr Pro Lys Lys Gln Gly Gln
                740                 745                 750
                                     C

ATC TCA GAA GAG TAT ATG CAA ACG GTT TTG TAA
Ile Ser Glu Glu Tyr Met Gln Thr Val Leu
755                 760
```

GTTAACACTACACTACTCACAATGGTAGGGGAACTTACAAAATAATAGTTT

FIG. 6D

TSH RECEPTOR

BACKGROUND OF THE INVENTION

This application is a continuation-in-part of U.S. Ser. No. 565,669, filed Aug. 10, 1990, abandoned, which in turn is a continuation-in-part of U.S. Ser. No. 469,925, filed Jan. 25, 1990, abandoned, both of which are hereby incorporated by reference herein which is itself a divisional application of Cone, U.S. Ser. No. 404,899, filed Sep. 8, 1989, entitled TSH RECEPTOR.

This invention concerns nucleic acid encoding a mammalian thyroid stimulating hormone (TSH, also known as thyrotropin) receptor, and purified mammalian TSH receptors.

The TSH receptor is a protein believed to be involved in a human autoimmune disease termed "Graves'" disease. It is believed that antibodies against the TSH receptor are made in patients suffering from this disease. These auto-antibodies are currently detected by providing radiolabeled TSH, and detecting blocking of binding of the TSH to crude porcine membranes thought to include a TSH receptor.

Rees Smith et al. (Endocrine Reviews 9:106, 1988) describes the structure of a TSH receptor and predicts that clones of DNA encoding such receptors can be isolated by determination of the amino acid sequence of the TSH receptor and subsequent use of oligonucleotide probes to identify clones in a library. The receptor was only purified to about 0.001% purity (i.e., 10 µg of TSH receptor in 1 g of protein.

SUMMARY OF THE INVENTION

Applicant has succeeded in isolating nucleic acid encoding at least two mammalian TSH receptors, and providing an expression system which enables production of large amounts of purified mammalian TSH receptor. Such purified receptor is useful in detection of auto-antibodies in patients suffering from Graves' disease or other malfunctions of the thyroid using simple antibody assays, such as a competitive radioimmune assay or an ELISA test.

In a first aspect, the invention features purified nucleic acid encoding a protein having the immunological or biological activity of a mammalian TSH receptor. The purified nucleic acid can be purified cDNA, or a purified vector including that nucleic acid. In a related aspect, the invention features purified, e.g., recombinant, protein having the immunological or biological activity of a mammalian TSH receptor.

By "immunological activity" is meant the ability to selectively form an immune complex with auto-antibodies to the TSH receptor. By "purified" is meant that the nucleic acid or protein is provided separated from contaminating nucleic acid or other cell components, such as proteins and carbohydrates, with which the naturally occurring nucleic acid encoding the receptor or receptor occurs. Most preferably, the nucleic acid is provided as a homogeneous solution separated from all cell components, or is the major nucleic acid present in a preparation. More preferably, the nucleic acid is provided within a vector which is resident within a cell in a manner which allows expression of the nucleic acid to provide sufficient TSH receptor to be useful in this invention. By "recombinant" is meant that the protein is expressed from nucleic acid which has been manipulated by recombinant DNA methodology to place it in a vector or chromosome at a location in which it does not naturally occur. Preferably the purified protein is present at a purity of at least 10% of the total protein in a preparation, or even at 50% or 90% purity.

The biological activity of mammalian TSH receptor is that activity naturally associated with the TSH receptor of mammals, i.e., the ability of that protein to recognize and interact with TSH. It preferably includes other biological activities of the TSH receptor such as activating adenylate cyclase, well known to those of ordinary skill in the art.

In preferred embodiments the TSH receptor is that receptor occurring in humans; the nucleic acid has a nucleotide sequence encoding an amino acid sequence identical to that of a naturally occurring mammalian TSH receptor, most preferably a human TSH receptor; or the nucleic acid encodes a protein having only conservative amino acid substitutions compared to a naturally occurring mammalian TSH receptor. Such conservative amino acid substitutions are well known to those skilled in the art and would include, for example, substitution of valine for glycine or leucine, substitution of a positively charged amino acid for another positively charged amino acid, or substitution of a negatively charged amino acid for another negatively charged amino acid. Such substitutions will not significantly affect the biological activity of the encoded TSH receptor; i.e., the biological activity of the substituted form will be at least 75% that of the naturally occurring form.

The proteins of the invention can be used in a method for detecting the presence of anti-TSH receptor antibodies in the serum of a patient. The method includes providing a purified TSH receptor as described above, and contacting that receptor with the serum. Reaction of the receptor with the serum is an indication of the presence of anti-TSH antibodies in that serum. This method may include any of many well known immunological procedures for detection of antibodies, such as ELISA, Western blot or competitive binding assays.

The present invention provides a sufficient amount of a mammalian TSH receptor to be useful for rapid testing of patients for the presence of anti-TSH receptor antibodies. It also provides sufficient receptor protein to allow analysis of the sequence of the protein. Such analysis will aid determination of specific epitopes on that protein to allow design of small homologous peptides which will block the activity of autoimmune antibodies. Those peptides will thus block overstimulation of the thyroid in patients, such as those suffering from Graves' disease. The invention also provides the tools necessary to allow development of agonists or antagonists of TSH binding to a mammalian TSH receptor. These antagonists will be useful for preventing hyperthyroidism due to elevated levels of TSH.

In another aspect, the invention features a method for determining the presence of TSH in a sample. The method includes providing a mammalian cell having DNA encoding biologically active TSH receptor, the cell expressing TSH receptor from the DNA under assay conditions; contacting the cell with the sample to cause TSH within the sample to contact the cell; and measuring the level of intracellular cyclic adenosine monophosphate prior to and after the contacting step. An elevated level of cyclic adenosine monophosphate after the contacting step compared to that prior to the contacting step is indicative of the presence of TSH within the cell.

Other features and advantages of the invention will be apparent from the following description of the preferred embodiments thereof, and from the claims.

DESCRIPTION OF THE PREFERRED EMBODIMENTS

The drawings will first briefly be described.

Drawings FIG. 1 is a depiction of the nucleotide base sequence of the rat LH receptor probe.

FIG. 2A–E is a depiction of the nucleotide base sequence of the human LH receptor cDNA and the derived amino acid sequence.

FIG. 5A–B is a depiction of the partial nucleotide base sequence of the bovine and human TSH receptors. The boxed sequences indicate regions with possible sequence errors due to compression during sequence determination.

FIG. 6A–D is a depiction of the nucleotide base sequence and the derived amino acid sequence of the human TSH receptor cDNA.

Figure 7:
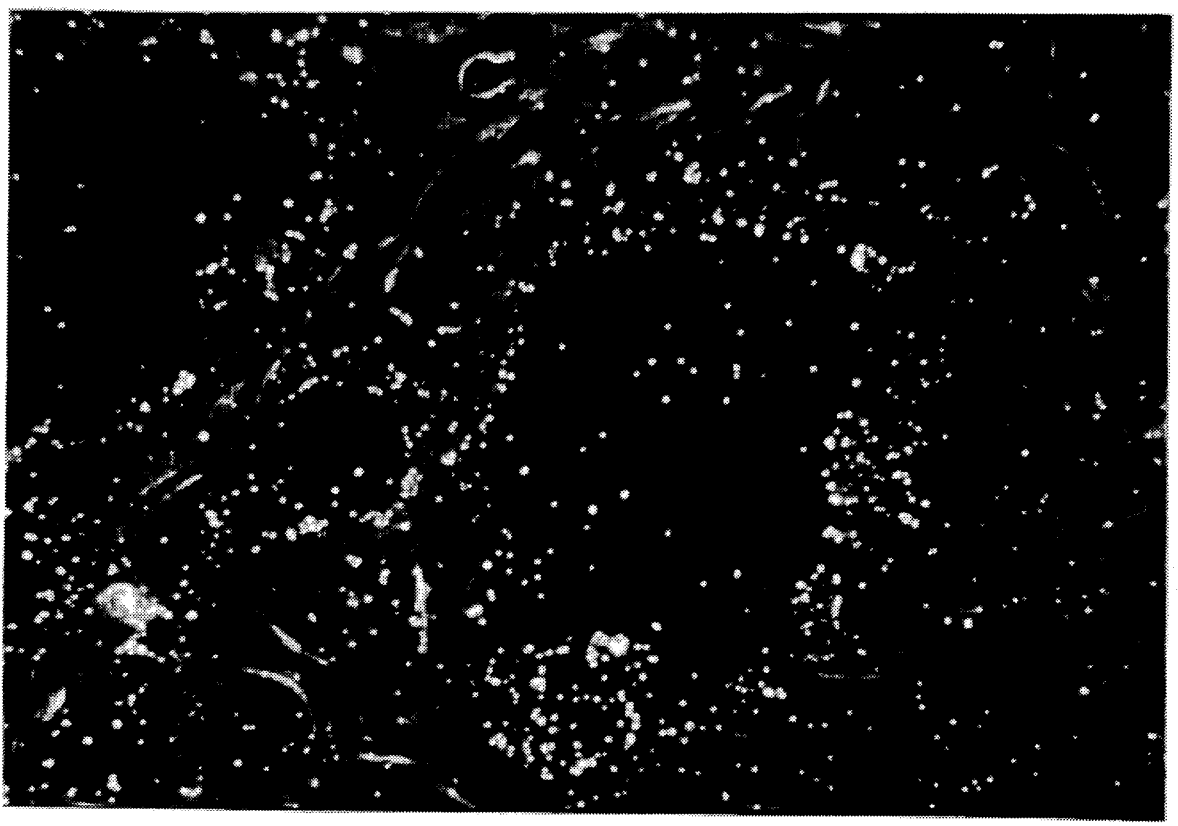

FIG. 7 illustrates a darkfield photomicrograph (75× magnification) showing an autoradiographic signal (bright spots) produced by radiolabeled anti-sense transcript of human TSH receptor overlying a haematoxylin and eosin stained section of human thyroid.

Figure 8:
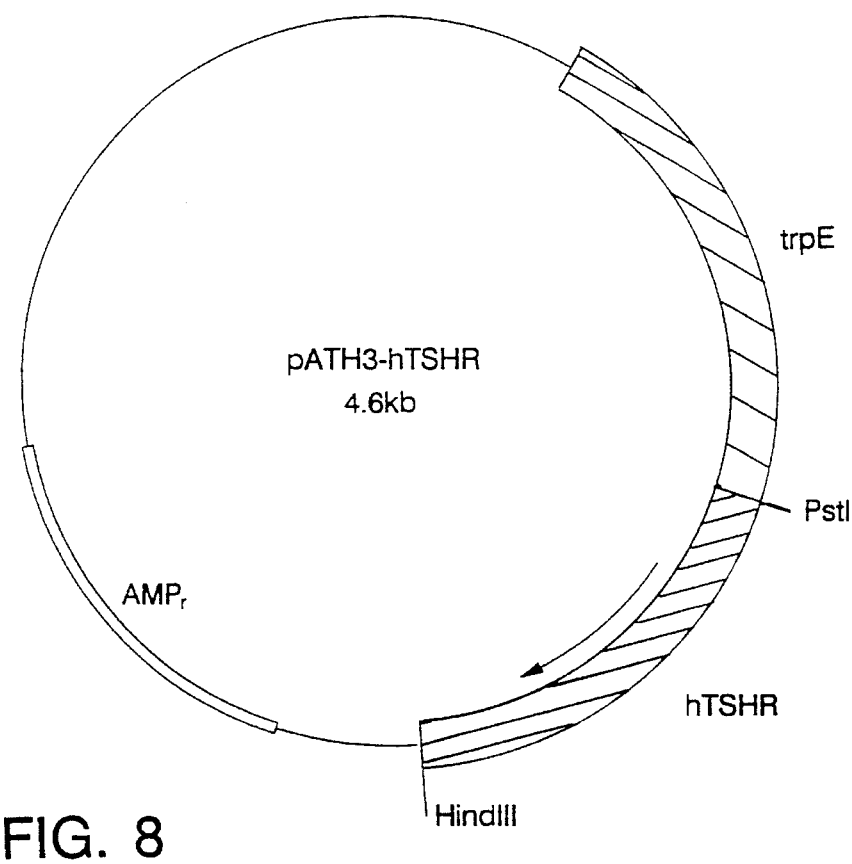

FIG. 8 is a diagrammatic representation of the pATH3-hTSHR expression vector.

Figure 9:
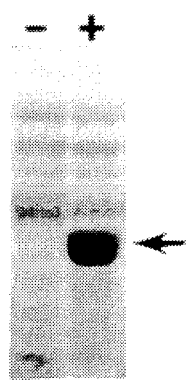

FIG. 9 illustrates a photograph of a polyacrylamide gel demonstrating the expression of the trp E-TSH receptor fusion protein (small arrow) in The absence (−) and presence (+) of indoleacetic acid. The small arrow indicates a protein of the size predicted for the fusion protein.

Figure 10:
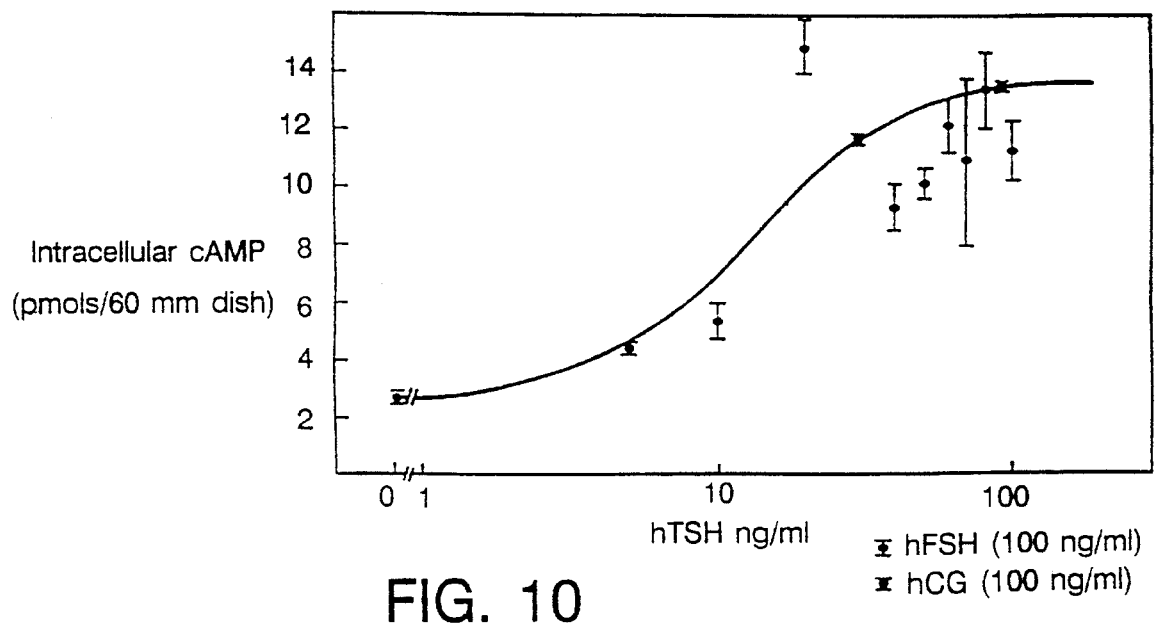

FIG. 10 is a graphical representation of the the level of intracellular cyclic adenosine monophosphate (cAMP) as a function of the concentration of applied hormone.

TSH RECEPTOR

TSH receptors useful in this invention include any such receptor isolated from a mammal, or any protein having the biological activity of such a receptor. Such proteins will include proteins derived from naturally occurring TSH receptors having one or more of their amino acids modified conservatively as discussed above. Such modification may be by any standard procedure, for example, by recombinant DNA technology. Generally, such receptors will be expressed by recombinant DNA technology by isolating the gene encoding that receptor, and placing that gene within an expression vector, after removing any intronic DNA that may be deleterious to expression of the full length receptor protein. Such expression vectors will include bacterial, fungal, insect, and mammalian expression vectors which may be expressed within a bacterial, fungal, insect, or mammalian cell by techniques well known to those with ordinary skill in the art. Purified mammalian TSH receptor may also be isolated by preparing antibodies to one of the above recombinant mammalian TSH receptors, and using those antibodies to immunoaffinity purify a naturally occurring TSH receptor. Generally, such a procedure is not preferred, since the yield of TSH receptor will be extremely small.

Once the desired TSH receptor protein is cloned, and its amino acid sequence determined, proteins having the biological activity of the receptor may be designed by standard procedure. For example, oligonucleotides may be synthesized by standard procedure, and inserted into any standard expression vector to cause expression of fragments of the naturally occurring TSH receptor. These fragments can be screened by standard procedure to determine whether they have the desired biological activity of the receptor protein. For example, it may be determined by affinity chromatography, Western blot analysis, or some equivalent analysis, whether that synthetic peptide is able to bind with antibodies against a TSH receptor. Those fragments which can bind are useful in this invention. Similarly, the expressed TSH receptor, or that purified as described above, may be fragmented by use of enzymes, e.g., trypsin, which specifically cleaves the amino acid sequence into smaller fragments. These fragments may then be tested in much the same way as the synthetic peptide fragments to determine their usefulness in methods of this invention.

Below is presented one example of a mammalian TSH receptor-encoding gene, and expression of that gene within a vector to provide a purified mammalian TSH receptor. This example is not limiting to the invention and those skilled in the art will recognize many other mammalian TSH receptors can be isolated by identical procedures, or by use of the cloned DNA provided as deposits in the American Type Culture Collection (see below). The DNA in these deposits may be used to screen any existing or newly constructed library of mammalian DNA to determine the presence of clones encoding a part or all of a mammalian TSH receptor. Preferably such libraries will be constructed as cDNA libraries from RNA present in the thyroid of a mammal.

Example: Human and Bovine TSH Receptor

A 622 nucleotide fragment of the rat luteinizing hormone (LH) receptor gene was obtained from Deborah Segaloff of the Center for Biological Research at the Population Counsel, New York, N.Y. 10021, and from Peter Seeburg at the University of Heidelberg. This DNA fragment was used as a probe of a lambda-gt11 cDNA library constructed from RNA isolated from the thyroid of a patient suffering from Graves' disease. The nucleotide base sequence of this probe is shown in FIG. 1.

The cDNA library was constructed generally as follows. RNA of the thyroid was isolated using a standard guanidium/thiocyanate procedure and reverse transcribed using the method of Gubler and Hoffman. The resulting cDNA was size selected using a Sepharose G50 gel filtration column to select cDNA of greater than 1 kb in size. The cDNA was methylated with EcoRI methylase, linked to EcoRl linkers, and then treated with EcoRI. The resulting DNA was ligated to EcoRI treated lambda-gt11 DNA. The resulting lambda DNA was amplified in *E. coli* strain 1090.

The rat LH gene fragment was labeled with $^{32}$P-dCTP and plates containing the lambda gt11 library screened on nitrocellulose filters at low stringency in 30% formamide, 1M NaCl, at 42° C. The filters were then washed at low stringency in 2×SSC at 50° C.

Two classes of clones were detected, one class giving a strong reaction, and the other class a faint reaction with the probe. The strongly reacting plaques were purified three times using standard procedure, and four were determined to encode overlapping parts of the same gene by restriction endonuclease mapping, and DNA sequencing procedures. The 5' terminal 600 nucleotides of the gene showed high homology to the rat LH receptor. Further analysis determined that the cDNA encoded the full length human LH receptor protein with several introns remaining. The nucleotide base sequence is provided in FIG. 2A–E. The amino acid sequence, molecular weight and isoelectric point of the encoded protein can be calculated by standard techniques from this sequence. The encoded protein has 90% homology in amino acid sequence to the rat LH receptor protein. The cDNA includes intronic DNA. RNA protection experiments, Northern analysis, and polymerase chain reaction experiments showed that the mRNA encoded by this clone is expressed in the thyroid, testes, and ovary, as well as in Graves' thyroid, and in thyroid cell lines. The RNA is expressed in the thyroid but is incompletely spliced. Thus, this clone does not encode thyroid specific DNA.

Figures 3, 4:
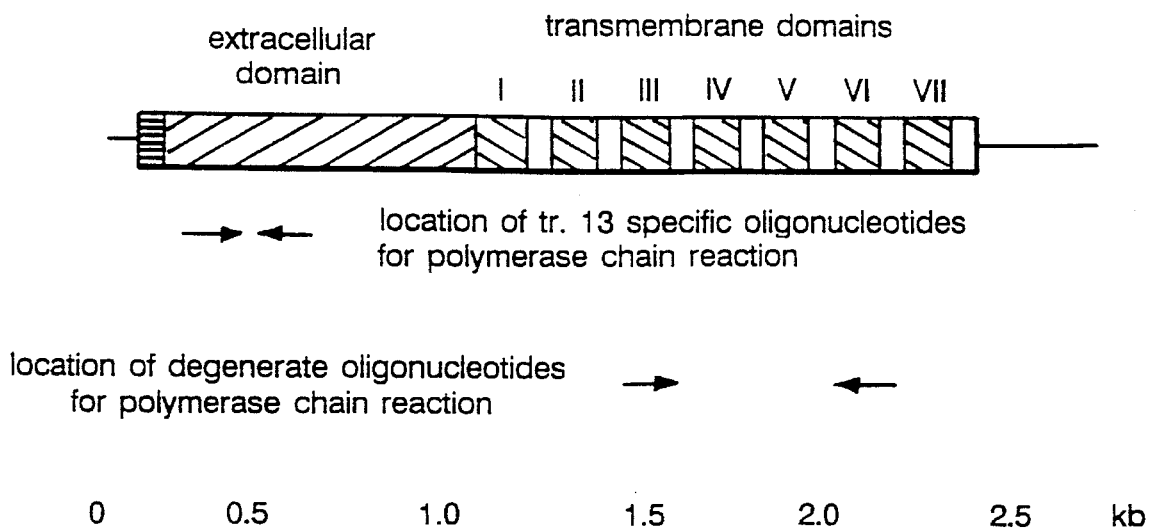
FIG. 3 is a diagrammatic representation of the structure of the human LH receptor-encoding gene and the derived amino acid sequence.
FIG. 4 is a depiction of the nucleotide base sequence of degenerate oligonucleotide probes based on the human LH receptor DNA sequence.

In order to isolate clones encoding a TSH receptor, two degenerate oligonucleotide probes were constructed, one having homology to the transmembrane domain III of the above cloned human LH receptor DNA and the other having homology to the transmembrane domain VI of the LH receptor DNA. These domains and the location of the probes are shown in FIG. 3. These domains are separated by a distance of approximately 400 nucleotides in the cDNA. The oligonucleotides were synthesized and purified by standard procedure; their sequences are shown in FIG. 4.

Total RNA was isolated from a human Graves' thyroid, and from a bovine thyroid sample. Ten µg of total RNA from these two samples was separately reversed-transcribed using Moloney murine leukemia virus reverse transcriptase (commercially available). First strand cDNA was synthesized in a 50 µl reaction, and 5 µl of the resulting cDNA used in a polymerase chain reaction with the above synthetic oligonucleotides. This reaction had a total volume of 100 µl, including 5 µl of cDNA, 500 picomoles of each oligonucleotide, and the standard buffers and nucleotides described by Cetus Corporation (Emeryville, Calif.) This reaction was treated at 94° C. for one minute in the presence of Taq DNA polymerase and then two minutes at 50° C. and three minutes at 72° C. This cycle of heating and cooling between 50° C. and 94° C. was repeated thirty times. At this point, no amplification product could be observed. Five µl of the resulting reaction was removed and the procedure repeated. At this point, a DNA product was observed. No such product was observed in reactions using total RNA isolated from osteosarcoma, testes, ovary, melanoma, or placenta. Thus, the DNA product appears to be thyroid specific. The resulting material was precipitated and resuspended by standard procedure, and digested with HindIII and EcoRI.

The EcoRI HindIII fragment was subcloned into the vector pBS⁻ (Strategene, La Jolla, Calif.), and transformed into *E. coli*. The resulting vector was sequenced by Sanger dideoxy procedures. Both human and bovine cDNAs were sequenced and found to encode a protein having about 84% homology. Their tentative sequences are presented in FIG. 5A–B. In contrast, the DNA had only about 68% homology with rat, porcine, and human LH receptor.

The fragments derived from the polymerase chain reaction were removed from the vector and labeled with $^{32}$p. These fragments were then used as probes to screen the above described lambda-gt11 library at high stringency. The conditions were 50% formamide at 42° C. in the presence of 1M NaCl for 15–20 hours, and then washing of the nitrocellulose filters at 20°–25° C. in 2×SSC for 15, minutes at 68° C. in 1×SSC for 45 minutes, and at 68° C. in 0.1×SSC for 45 minutes. Strongly hybridizing plaques were detected at a higher frequency than had been detected for the LH receptor clones. Twelve of these plaques were purified three times, purified DNA isolated from six, and analyzed by EcoRI restriction analysis. Four of these clones contained inserts of approximately 4.2 kb. These inserts were inserted into the pBS⁻ vector Northern blot analysis using the resulting clones showed that the DNA hybridized to RNA expressed only in the thyroid in both Graves' patients and the cold nodule sample, but not in the testes, ovary or other tissues. The DNA hybridized with an RNA of approximately 4.2 kb and thus appears to represent a full length clone of the human TSH receptor. This RNA has a 3'-untranslated sequence of between 2 and 2.5 kb, and a 5'-untranslated sequence of approximately 50 bases. One clone, TR.12.6-1 (hTSH receptor), has been determined, by DNA sequencing, to contain a full length human TSH receptor cDNA (FIG. 6A–D).

The molecular weight of the protein of the human TSH receptor estimated from the primary amino acid sequence shown in FIG. 6 is 86,738, or, experimental errors allowed, 86,634+/−150. Similarly, the isoelectric point of the protein is estimated to be 6.55, or, experimental errors allowed, 6.42+/−0.15.

Further proof that the clone encoded human TSH receptor was provided by in situ hybridization histochemistry which demonstrated specific hybridization of anti-sense human TSH receptor probe to thyroid follicular cells which are known to respond to TSH (FIG. 7). Briefly, 8 µm cryostat sections of normal appearing thyroid follicles were prepared for in situ hybridization. A 1 kb fragment of cDNA encoding the human TSH receptor was used to prepare $^{35}$S labelled anti-sense transcript. Tissue sections were pre-treated with detergent and protease, and then incubated in hybridization buffer for 16 hours at 42° C. with 3×10⁵ CPM (specific activity approximately 10⁸ cpm/µg) of probe as described (Hoefler et al., Histochem, J. 18:5597, 1986).

The above-described cDNA from human and bovine, or any other mammal may be expressed by standard procedures to provide large quantities of TSH receptor. For example, the above cDNA may be inserted into a trp E-fusion plasmid, e.g., pATH-1, 2, or 3, to form a stable hybrid protein with the Trp E protein. Alternatively, the cDNA may be inserted into a mammalian expression system such as a cytomegalovirus or retrovirus vector. Glycosylated protein will result when the DNA is expressed in the mammalian expression system.

Below is presented an example of a method to express TSH receptor. The amino terminal coding sequence of the human TSH receptor from a PstI site (nucleotide 346) to a HindIII site (nucleotide 1213) was ligated to PstI/HindIII digested pATH3. The resulting plasmid, pATH3-HTSHR (FIG. 8), expresses a 66 kD fusion protein containing approximately 37 kD of the *E. coli* Trp E protein fused to 29 kD of the amino terminus of human TSH receptor protein. DH5α *E. coli* transformed with pATH3-hTSHR were grown in selective M9 media for 2 hours in either the absence or presence of 40 µg/µl indoleacetic acid, an inducer of the Trp E gene. Bacterial pellets were lysed in SDS loading buffer and ⅒th of the material was electrophoresed on a 10% polyacrylamide Laemmeli gel (FIG. 9).

Examples of a biologically active preparation of human TSH receptor within this invention include, but are not limited to, transformed or transfected mammalian cells expressing human TSH receptor (e.g., see FIG. 10 and its accompanying text, infra) and purified human TSH receptor. By "biologically active" is meant the capability of the preparation to bind human TSH. Because of the extremely small quantities of human TSH receptor in its natural sources, human TSH receptor of this invention is purified from transformed or transfected mammalian cells which express such receptor, and is therefore free of cell components associated with naturally-occurring human TSH receptor regardless of the degree of purification.

The following is a procedural guideline for the purification of TSH receptor to homogeneity. It is based on methods which have been used successfully for the complete or partial purification of receptors and integral membrane proteins. See, e.g., Supattapone et al., J. Biol. Chem. 263:1530 (1987) and Rickards et al., FEBS Letters 127:17 (1981), both of which are hereby incorporated by reference.

As a first step, cells expressing the TSH receptor are pelleted by low speed centrifugation and resuspended in a hypotonic buffer (preferably a lowmolarity neutral pH buffer containing sub isotonic levels of salts and a combination of protease inhibitors) in order to lyse the cells. After a short incubation of the cells in this buffer on ice, the cells are further disrupted by homogenization using either mechanical or sonic methods to obtain an even suspension of fine particulate cellular matter. Organelles and other cellular debris are removed by low speed centrifugation. The supernatant is then centrifuged at high speed (for example, 100000× g) to pellet the membranes.

At this point, a method known as "alkaline stripping" can be used to remove proteins that are only loosely associated with the membrane. This involves quickly washing the membrane preparation by resuspension in either an EDTA solution at alkaline pH or a dilute NaOH solution on ice and then repelleting by high speed centrifugation.

The membrane preparation is solubilized by incubation on ice with gentle agitation of the sample in a neutral buffer containing protease inhibitors and an appropriate detergent (such as 0.5% Triton x-100 or 1% CHAPSO for example). After a high speed centrifugation to remove nonsoluble debris, the supernatant containing solubilized TSH receptor is further processed over a series of chromatography columns to obtain purified receptor.

The first of these columns is a TSH affinity column. This column is prepared by covalently coupling purified TSH to a resin such as CNBr-activated sepharose using standard methodologies provided by the manufacturer. The column is equilibrated with a neutral buffer at low ionic strength in the presence of lower levels of the detergent used for membrane solubilization. The soluble membrane protein preparation which contains the TSH receptor is passed over this column. The column is then washed extensively with the equilibration buffer containing low levels of salt in order to remove any nonspecifically bound proteins. The salt concentration is then increased for the specific elution of the TSH-binding proteins which include the TSH receptor. Alternatively, the specifically bound proteins can be eluted with an acidic or alkaline buffer.

The few remaining contaminating proteins can then be removed using an anion exchange column (such as DEAE or Q-sepharose) in the presence of a nonionic detergent. The pH and the ionic strength of the TSH column elution are adjusted to levels at which the TSH receptor will bind to the anion exchange resin. The TSH receptor is eluted from the column and purified from other contaminating proteins using a gradient of increasing ionic strength buffers.

A final purification and buffer exchange of the TSH receptor into the storage buffer of choice can be achieved on a size exclusion chromatography column (such as Sephacryl S-200). The column is equilibrated using the final storage buffer containing detergent. The TSH receptor eluted from the anion exchange column is loaded onto the size exclusion column and fractions of the column eluant are collected. Those fractions containing TSH receptor are pooled and stored for any future applications.

Use

As discussed above, nucleic acid encoding TSH receptor may be used to express large quantities of TSH receptor. For example, high level expression is achieved with a Baculovirus vector pVL941, the *E. coli* vector paTH3, and the mammalian vector pLJ. Such protein is useful for detection of auto-antibodies found in Graves' patients. This allows determination of the state of the thyroid of those patients, and indicates the progress of that patient. This test may be performed in an ELISA format, for example, in a dipstick assay. The test might also take the form of a competitive binding assay employing radiolabeled TSH and TSH receptor. Such assays are extremely sensitive, and more readily performed than prior methods of detecting such antibodies.

The expressed protein is useful for defining the epitopes recognized by antibodies in Graves' patients. This analysis may be performed by standard procedure, for example, by expressing portions of the cloned DNA to provide partial TSH receptor fragments, or by fragmenting the expressed receptor protein as discussed above. Once the region recognized by such antibodies is defined, these fragments may be used in immunoassay procedures. In addition, definition of epitopes may be performed by manipulating the cloned genes using standard techniques of molecular biology to provide proteins in which one or more amino acids which may form a part of one or more epitopes of the protein is altered or deleted.

The protein or portions thereof is also useful as a therapeutic where it may be administered in a pharmaceutically acceptable compound at a sufficient dose to alleviate one or more symptoms of Grave's patients, or other patients suffering from thyroid malfunction. Generally, such administration will be at level between one and one thousand micrograms per kilogram of patient.

Small peptides may be designed which will block the activity of auto-antibodies that act as TSH agonists, and thus block stimulation of the thyroid. Other small peptides may be designed which will block auto-antibodies that act as TSH antagonists. In addition, antagonists of TSH may be constructed which prevent binding of TSH to the TSH receptor and thus prevent elevated thyroid activity.

Assays for TSH

There follows two assays for TSH. The first assay technique is based upon the expression of TSH receptor within a cell which does not naturally contains such a receptor. This cell, when contacted with TSH, will increase expression of cyclic adenosine monophosphate, which can be detected as a measure of the amount of TSH in a sample.

In this assay, the human TSH receptor-encoding DNA is inserted with a mammalian retroviral vector pLJ at the BamHI to SalI sites. The resulting vector is then transfected into human 293 cells and clonal cell lines containing the vector isolated by selection in the presence of the antibiotic G418. Such transfection causes the cells to become responsive to TSH as measured by the activation of adenylate cyclase and accumulation of cAMP following treatment with TSH. Thus, these cell lines provide a highly sensitive assay system for the hormone TSH. Cells in culture or cell membrane preparations may be exposed to the sample thought to contain TSH and the resulting adenylate cyclase activity quantitated and correlated with the cyclase activity from standard dilution curves of TSH in order to calculate the concentration of TSH in a sample. Concentrations as low as 1 ng/ml or even 0.1 ng/ml can be detected in this assay. This assay demonstrates that the TSH receptor encoded by the cDNA described above is biologically active and leads to specific TSH responsiveness in a previously unresponsive cell line. These cell lines are responsive not only to naturally occurring TSH but also to recombinant TSH.

Specifically, a retrovirus expression vector pLJ (Korman et al., Proc. Natl. Acad. Sci. USA 84:2150, 1987) containing the entire tr.12 cDNA sequence was transfected into human 293 cells and intracellular cAMP concentrations measured 60 hours later using a $^3$H-cAMP displacement assay after treatment with hCG, hFSH, or hTSH. Referring to FIG. 10, 100 ng/ml of hFSH or hCG has little effect while the same amount of hTSH elevated intracellular cAMP over 6-fold. Half maximal intracellular concentrations of cAMP were obtained with approximately 60 picomolar hTSH. In several experiments, a 15-fold elevation of intracellular cAMP was induced by application of 100 ng/ml hTSH. Transfection of the retrovirus vector alone, with no hTSH-r insert, produced no elevation of intracellular cAMP over background in cells treated with 100 ng/ml TSH. Expression of the human LH/CG receptor was attempted using identical methods, however, no elevation of cAMP was seen after treatment with any of the glycoprotein hormones. This could result from any of number of problems, including, for example, the deletion found in clone tr.13, or perhaps inefficient removal of the LH/CG-R introns in the non-gonadal 293 cell line.

The TSH receptor of this invention can be used to measure TSH by means of a competitive binding assay. In this assay TSH receptor, or a portion thereof capable of binding TSH, is immobilized on a support matrix. The immobilized receptor is incubated with excess TSH, which has been tagged with a radioactive or florescent label, long enough for the binding reaction to come to equilibrium. Unbound TSH is removed by a washing step, and the receptor is incubated with the test sample. Once this second binding step has come to equilibrium, the immobilized receptor is washed again. The amount of tagged TSH displace by TSH in the test sample then serves as a measure of the TSH present in the test sample. Other assays for TSH employing purified TSH receptor can be devised by those skilled in the art.

Deposits

The following DNA deposits were made on Sep. 6, 1989, with the American Type Culture Collection (ATCC) 12301 Parklawn Drive, Rockville, Md. 28052 under the terms of the Budapest Treaty, where the deposits were given the following accession numbers:

| Deposit | Accession No. |
|---|---|
| tr.12.6-1 (hTSH receptor) | 40651 |
| tr.13.t35 (hLH receptor) | 40652 |

Applicant's assignee, New England Medical Center Hospitals, Inc., represents that the ATCC is a depository affording permanence of the deposit and ready accessibility thereto by the public if a patent is granted. All restrictions on the availability to the public of the material so deposited will be irrevocably removed upon the granting of a patent. The material will be available during the pendency of the patent application to one determined by the Commissioner to be entitled thereto under 37 CFR 1.14 and 35 USC 122. The deposited material will be maintained with all the care necessary to keep it viable and uncontaminated for a period of at least five years after the most recent request for the furnishing of a sample of the deposited microorganism, and in any case, for a period of at least thirty (30) years after the date of deposit or for the enforceable life of the patent, Whichever period is longer. Applicants' assignee acknowledge its duty to replace the deposit should the depository be unable to furnish a sample when requested due to the condition of the deposit.

Other embodiments are within the following claims

I claim:

1. A biologically active preparation of human TSH receptor which is free of cell components associated with naturally-occurring human TSH receptor, said receptor comprising the amino acid sequence set out in FIG. 6.

2. The preparation of claim 1, wherein said receptor has a molecular weight of 86,738.

3. The preparation of claim 2, wherein said receptor has an isoelectric point of 6.55.

4. The preparation of claim 1, wherein said receptor has an isoelectric point of 6.55.

5. The preparation of claim 1, wherein said preparation comprises mammalian cells into which an exogenous DNA sequence encoding human TSH receptor is introduced so that said cells express biologically active TSH receptor.

6. The preparation of claim 5, wherein said receptor has a molecular weight of 86,738.

7. The preparation of claim 6, wherein said receptor has an isoelectric point of 6.55.

8. The preparation of claim 5, wherein said receptor has an isoelectric point of 6.55.

9. A method for detecting the presence of anti-human TSH receptor antibodies in the serum of a patient, comprising the steps of:

provi ding a biologically active human TSH receptor preparation which is free of cell components associated with naturally-occurring human TSH receptor, said receptor comprising the amino acid sequence set out in FIG. 6, contacting said TSH receptor preparation with the serum; and detecting reaction of said serum as an indication of the presence of antibodies in the serum.

10. The method of claim 9, wherein said receptor has a molecular weight of 86,738.

11. The preparation of claim 10, wherein said receptor has an isoelectric point of 6.55.

12. The method of claim 9, wherein said receptor has an isoelectric point of 6.55.

13. A method for determining the presence of human TSH in a sample comprising the steps of:

providing a mammalian cell comprising an exogenous DNA sequence encoding biologically active human TSH receptor, said receptor comprising the amino acid sequence set out in FIG. 6, and said cell expressing TSH receptor from said DNA under assay conditions;

contacting said cell with said sample to cause TSH within said sample to contact said cell; and measuring the level of intercellular cyclic adenosine monophosphate prior to and after said contacting step;

wherein an elevated level of cyclic adenosine monophosphate after said contacting step is indicative of the presence of TSH in said sample.

* * * * *